(12) United States Patent
Ryu

(10) Patent No.: US 7,378,540 B2
(45) Date of Patent: *May 27, 2008

(54) PROCESS FOR PRODUCING ORGANIC CARBONATES

(75) Inventor: J. Yong Ryu, League City, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 122 days.

This patent is subject to a terminal disclaimer.

(21) Appl. No.: 11/256,394

(22) Filed: Oct. 21, 2005

(65) Prior Publication Data

US 2007/0093672 A1     Apr. 26, 2007

(51) Int. Cl.
  *C07C 69/96*  (2006.01)
(52) U.S. Cl. ...................................... 558/274
(58) Field of Classification Search ................. 558/274
  See application file for complete search history.

(56) References Cited

U.S. PATENT DOCUMENTS 4,982,003 A    1/1991   Hara et al.
6,008,399 A    12/1999  Chang et al.
2007/0112214 A1  5/2007  Ryu et al.

OTHER PUBLICATIONS

Zhao et al. Materials Today 2006, 9(3), 32-39.*
Notification of Transmittal of International Search Report and Written Opinion of the International Searching Authority for International Application PCT/US06/33943 mailed Jul. 9, 2007 (7 pages).

* cited by examiner

*Primary Examiner*—Rebecca L Anderson
*Assistant Examiner*—Jason M Nolan
(74) *Attorney, Agent, or Firm*—Osha Liang LLP

(57) ABSTRACT

A process for producing various organic carbonates by performing transesterification and disproportionation reactions in dual vapor/liquid phase mode preferably in the presence of solid catalyst composition selected from the group consisting of oxides, hydroxides, oxyhydroxides or alkoxides of two to four elements from Group IV, V and VI of the Periodic Table supported on porous material which has surface hydroxyl groups and the method of reactivating catalyst deactivated by polymer deposition by contacting the deactivated catalyst with a solution of hydroxy containing compound in a solvent such as benzene or THF.

17 Claims, 1 Drawing Sheet

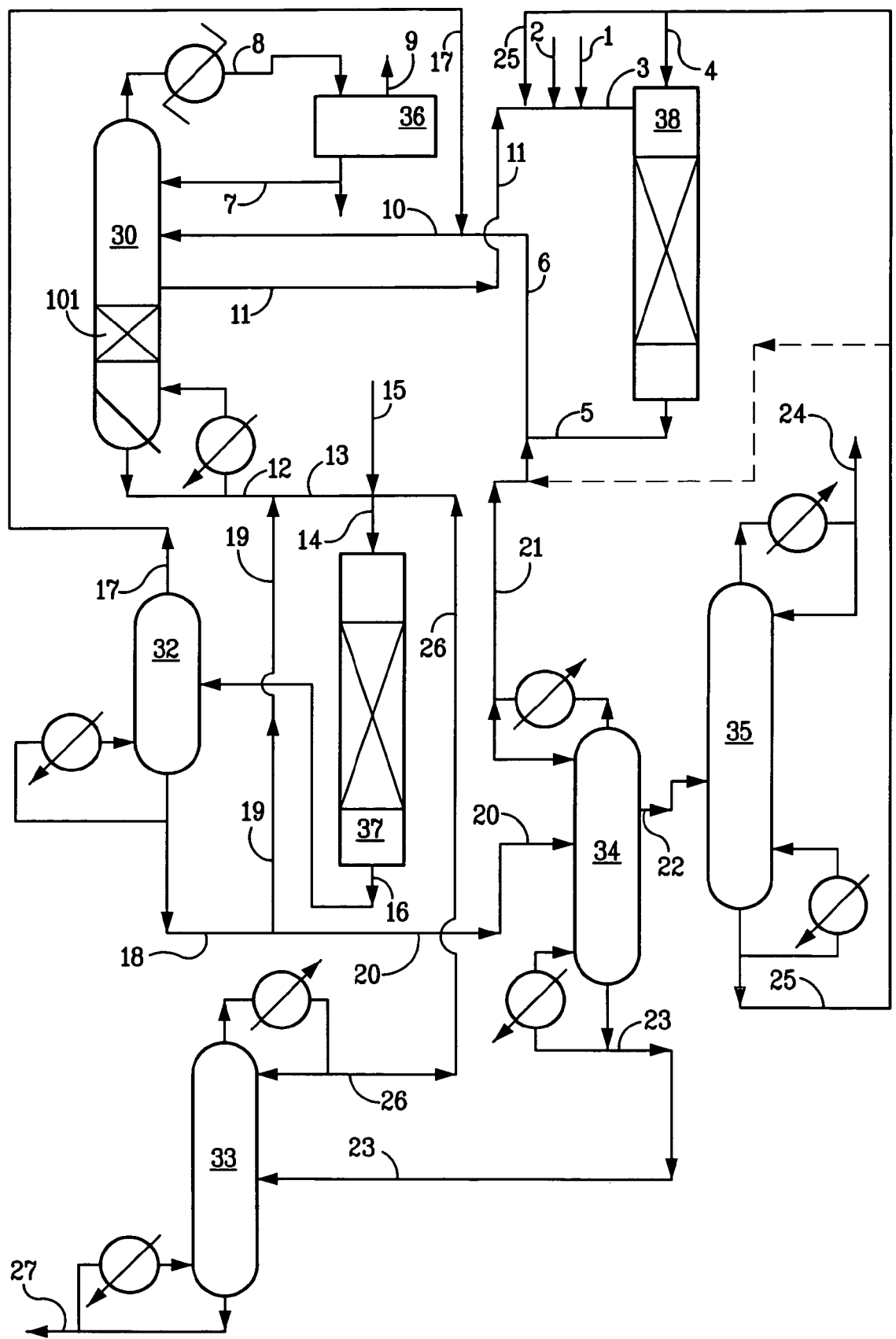

PROCESS FOR PRODUCING ORGANIC CARBONATES

BACKGROUND OF THE INVENTION

1. Field of the invention

The present invention relates to the process of producing various organic carbonates by performing chemical reactions, which are limited by equilibrium, and separating various chemical compounds involved. Achieving higher conversion than equilibrium condition is highly desirable for better economic reward. This invention discloses a method of shifting the equilibrium position of a chemical reaction to achieve higher conversion.

2. Related information

Diaryl carbonates, for example diphenyl carbonate (DPC), are an important raw material for the production of polycarbonates. The current state of the art produces DPC from dimethyl carbonate (DMC) and phenol in two steps by employing multiple reactors and a homogeneous catalyst, such as titanium alkoxide. The following three reactions are involved in producing DPC.

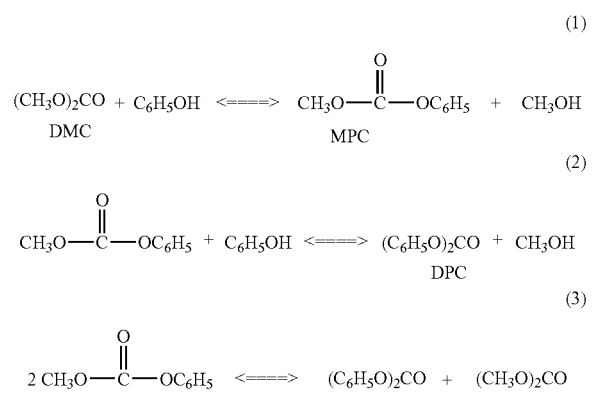

The equilibrium for each of the above reactions lies on far left side, whereas it is an object of the present invention that the equilibriums are moved to the right.

J. L. R. Williams et al. (J. Org. Chem., 24 (1) pp. 64-68, 1959) discovered that disproportionation of unsymmetrical carbonates such as methyl phenyl carbonate (MPC) and symmetrical carbonates such as dibenzyl carbonate can be performed in the presence of a suitable homogeneous catalyst, particularly metal alkoxide. However, the reaction accompanies a number of undesired side reactions such as decomposition of carbonate compounds to carbon dioxide, polymerization, formation of olefins, and ethers. The authors conclude that the course of the reactions depends on the structure of the carbonates and on the catalyst and the more alkaline catalysts promote more side reactions for the disproportionation of alkyl phenyl carbonates than mildly acidic catalyst such as titanium butoxide. Alkyl phenyl ether is the major undesired by-product.

U.S. Pat. No. 4,045,464 (1977) discloses a process for preparing diaryl carbonates from phenyl alkyl carbonates via the Reaction (3) in the presence of homogeneous Lewis acid catalysts of the formula $AlX_3$, $TiX_3$, $UX_4$, $TiX_4$, $VOX_3$, $VX_5$, and $SnX_4$, where X is a halogen, acetoxy, alkoxy or aryloxy group. DPC was produced by performing the disproportionation of ethyl phenyl (EPC) or MPC at 180° C. with 95% selectivity in the presence of homogeneous titanium catalysts.

U.S. Pat. No. 4,554,110 (1985) discloses an improved process for the preparation of aromatic carbonates from a dialkyl carbonate and phenol in the presence of catalyst comprising polymeric tin compounds. Diaryl carbonates are prepared by performing disproportionation of alky aryl carbonate.

U.S. Pat. No. 5,210,268 (1993) discloses a process for producing diaryl carbonates by performing various transesterification reactions in two reaction zones. An aromatic carbonate mixture is prepared by a transesterification reaction between a dialkyl carbonate, an alkyl aryl carbonate and a mixture thereof, and an aromatic hydroxy compound in the first step. A diaryl carbonate is produced by primarily performing disproportionation of alkyl aryl carbonate in the second step. The patent discloses the method of overcoming unfavorable equilibrium. The transesterification is performed in reactive distillation mode by feeding reactants to continuous multistage distillation columns in the presence of a homogeneous catalyst or a solid catalyst, while continuously withdrawing the produced aromatic carbonate mixture as a high boiling point product from a lower portion of the distillation column and continuously withdrawing light coproducts such as aliphatic alcohol or dialkyl carbonate as vapor stream from upper portion of the distillation columns. The disproportionation of alkyl aryl carbonate to diaryl carbonate and dialkyl carbonate is also performed in similar fashion. Diaryl carbonate is continuously produced by performing transesterification and disproportionation in sequence, utilizing multiple multi-stage distillation columns.

U.S. Pat. Nos. 5,872,275 (1999) and 6,262,210 (2001) disclose for the process producing diary carbonate from dialkyl carbonate and an aromatic hydroxy compound in the presence of liquid homogeneous catalyst and methods removing heavy high boiling point byproducts and regenerating catalyst for recycle.

U.S. Pat. No. 6,093,842 (2000) discloses the process producing diaryl carbonate from a dialkyl carbonate, an aromatic hydroxy compound and a mixed solution containing alkyl aryl carbonate by introducing three reactant streams into an extractive/reactive distillation column in the presence of a catalyst. Examples of the catalysts are lead compounds, copper compounds, alkali metal compounds, nickel compounds, zirconium compounds, titanium compounds, vanadium compounds, etc. The by-products are CO2, anisole, benzoates and heavy materials.

U.S. Pat. No. 5,426,207 (1995) discloses the process producing a diaryl carbonate such as DPC by conducting transesterification of DMC with an aromatic hydroxy compound and disproportionation of alkyl aryl carbonate in presence of a homogeneous catalyst in three successive reaction zones. Conditions are selected to maximize formation of alkyl aryl carbonate in the first and second reaction zones, while disproportionation is favored in the third reaction zone.

U.S. Pat. No. 6,767,517 (2004) discloses a process for the continuous production of diaryl carbonates. The process uses three reactive distillation column reactors and two rectification columns for the separation of intermediate reaction product and final product.

To alleviate shortcomings associated with using homogeneous catalysts for the production of diaryl carbonates, U.S. Pat. Nos. 5,354,923 (1994) and 5,565,605 (1996), and WO 03/066569 (2003) disclose heterogeneous catalysts.

WO 03/066569 discloses a process continuously producing an aromatic carbonate such as DPC in the presence of a heterogeneous catalyst prepared by supporting titanium oxide on silica (3 mm diameter) in two steps.

JP 79,125,617 (1979) and JP Application NO HEI 07[1995]-6682 discloses heterogeneous catalysts for the preparation of diphenyl carbonate by transesterification of DMC with phenol to MPC and disproportionation of MPC to DPC in the presence of $MoO_3$ or $V_2O_5$ supported on an inorganic support such as silica, zirconia or titania. The transesterification and disproportionation are carried out in a reactor-distillation tower consisting of a reactor and distillation tower with removal of the co-products by distillation.

The publication by Z.-H. Fu et al. (J Mol. Catal. A: Chemical 118, (1997) pp. 293-299) reports the synthesis of diphenyl carbonate from DMC and phenol in the presence of various heterogeneous metal oxide catalysts. The best selectivity is reported for the $MoO_3$ (20 wt. % optimum loading) catalyst supported on silica.

Due to many shortcomings of current DPC processes, an improved process is highly desired for saving materials, cheaper construction cost, consuming less energy, and plant operation cost. Although the prior art does not address catalyst life, all heterogeneous catalysts eventually deactivate and become useless. Heterogeneous catalysts are only practical in commercial use, if their cycle and service times are long enough or the catalysts can be rejuvenated insitu without serious financial cost. Thus, the issues of the catalyst deactivation and method of regeneration remain as substantial bars to the commercial application of the prior art.

SUMMARY OF THE INVENTION

This invention relates to a process for producing various organic carbonates by performing transesterification and disproportionation reactions in the presence of solid catalyst in dual phase reactor. The present process is beneficial for performing equilibrium limited chemical reactions involving organic carbonates, where both gas phase and liquid phase must coexist to shift the equilibrium position to right side of an equilibrium reaction, thereby resulting in high conversion. The chemical reactions are performed in the presence of one or multiple heterogeneous catalysts.

The preferred solid catalysts disclosed in this invention are mixed oxide catalysts composed of two to four different elements from Group IV, V and VI of the Periodic Table, preferably Ti, Zr, Hf, Nb, Ta, Mo, V, Bi and Si supported on porous materials such as silica, which have surface hydroxyl groups. Supported metal alkoxide or mixed metal alkoxide catalysts of the Group IV and V metal alkoxides, such as titanium alkoxides, zirconium alkoxides, vanadium alkoxides, niobium alkoxides, $VO(OR)_3$ or oligomers of oxoalkoxide, and the like constitute a preferred catalyst group. The transesterification catalyst and the disproportionation catalyst utilized in the present process may be the same or different.

In general, heterogeneous catalysts are more desirable compared to homogeneous catalyst, because of difficulties involved in recycling homogeneous catalysts. However, all heterogeneous catalysts eventually deactivate. Deactivated catalysts must be replaced either with fresh catalyst or regenerated insitu without too much difficulty.

For the purposes of the present invention, the term "dual phase mode" means any process having both a liquid and a vapor phase present in the reaction zone regardless of the means of achieving the vapor and liquid phases including "reactive distillation", "catalytic distillation", boiling and concurrent reaction and fractional distillation in a column. The term "treated support" or "treated silica" is understood to mean a support having an optimized population of surface hydroxyl groups for a given surface area for the preparation of the catalysts described herein.

In a preferred embodiment the process for the production of diaryl carbonate comprises;

(a) a plurality of reaction zones comprising a primary and a secondary reaction zone;

(b) supplying to said primary reaction zone a dialkyl carbonate and an aromatic hydroxy compound;

(c) maintaining the primary reaction zone under dual phase and reaction conditions conducive for the formation of alkyl aryl carbonate;

(d) transesterifying the dialkyl carbonate with the aromatic hydroxy compound in the presence of a solid catalyst selected from the group consisting of two to four elements from Group IV, V and VI of the Periodic Table supported on porous material which have surface hydroxyl groups;

(e) recovering a dual phase product stream from the primary reaction zone;

(f) separating the dual phase product stream from (e) to recover vaporous alkyl alcohol and liquid alkyl aryl carbonate;

(g) maintaining the secondary reaction zone under dual phase and reaction conditions conducive for the disproportionation of alkyl aryl carbonate to diaryl carbonate;

(h) disproportionating the alkyl aryl carbonate in the presence of a solid catalyst selected from the group consisting of two to four elements from Group IV, V and VI of the Periodic Table supported on porous material which have surface hydroxyl groups;

(i) recovering a dual phase product stream from the secondary reaction zone; and (j) separating the dual phase product stream from (i) to recover a vaporous component comprising aryl alkyl carbonate and liquid product comprising diaryl carbonate.

More preferably additional steps are carried out:

(k) separating diaryl carbonate by distillation and (l) recycling the aryl alkyl carbonate to the secondary reaction zone.

It is important that a support should have surface hydroxyl groups. Silica is a preferred support. Preferably the support is a treated support.

BRIEF DESCRIPTION OF THE DRAWING

The FIGURE is schematic representation of one embodiment of the process of the present invention.

DETAILED DESCRIPTION

The process improvements were made by introducing dual phase reactors to perform transesterification and disproportionation to establish the following process conditions for the production of DPC:

(1) feeding essentially an ethanol-free stream to the transesterification reactor;

(2) minimizing DEC in the feed stream to the disproportionation reactor;

(3) performing the transesterification in the presence of phenol such that the phenol to EPC mole ratio be greater than 0.2, preferably greater than about 0.3, most preferably greater than about 0.35;

(4) performing the disproportionation in the presence of phenol at phenol to DPC mole ratio of in the range of 0.05 to 10, preferably from 0.1 to 6 and phenol to EPC mole ratio of from 0.01 to 6;

(5) optionally introducing a trace amount of water into the disproportionation catalytic reaction zone in an amount up to 0.3 wt %, preferably up to 0.1 wt %, (6) capitalizing on the absence of a DEC/ethanol azeotrope to separate DEC from ethanol;

(7) essentially eliminating cold spots in the catalytic reaction zones;

(8) eliminating catalyst recycle, catalyst separation, and continuous addition of make-up catalyst;

(9) effective mixing of reactants and products; and

(10) preferably maintaining the presence of both vapor and liquid phases in the reaction zones to remove a low boiling reaction product into a gas phase to obtain high conversion, not limited by equilibrium constant.

The fixed bed reactors are operated in the dual phase mode, which means coexistence of both vapor and liquid in the reaction zones creating a boiling condition in the catalytic reaction zone of a dual phase reactor is desirable. Nevertheless, operating dual phase reactor under boiling condition is not necessary as long as both gas and liquid phases coexist in the reaction zone.

The flow direction in a dual phase reactor can be either down-flow or up-flow. Down-flow is preferred. Also the fixed bed dual phase reactors have recycle loops. A down-flow boiling point reactor is operated preferably to have a negative pressure drop, which means a lower pressure at the bottom of the catalyst bed than the top of the catalyst bed. The negative pressure drop is created by high mass flow rate of vapor-liquid mixture through a fixed heterogeneous catalyst bed in catalytic reaction zone. The negative pressure drop is desirable but not necessary. A pressure drop of approximately 0.2 psi per ft or more is preferable.

Operation of a dual phase reactor under boiling point condition has several advantages over the operation of a traditional fixed bed reactor, namely:

mass transport of the reactants from the bulk phase into the catalyst particles and transport of the reaction products from the inside pores of shaped catalyst pallets in the catalytic reaction zone, lateral mixing of the reactants and products in bulk phase, development of no or negligible temperature drop or hot spot in a catalytic reaction zone for either endo- or exothermic reaction, and removing light reaction products from the liquid reaction medium into gas phase, which results in a favorable equilibrium direction.

At a given reaction temperature and flow rate in the catalytic reaction zone, the boiling reaction condition in catalytic reaction zone is created by controlling the pressure, which is determined by the composition of the reaction medium. Optionally one may choose to use a lower boiling solvent to create better boiling condition in the catalytic reaction zone, when the boiling point of reactant or product is close to or higher than intended reaction temperature.

This invention is particularly useful for reactions where the boiling point of reaction product is higher than reaction temperature or too close to reaction temperature such that there will be no or insufficient gas phase volume in the reaction zone under the reaction condition. Examples of such a reaction include producing diphenyl carbonate by disproportionation of ethylphenyl carbonate or methyl phenyl carbonate or producing bis-(2-ethyl-1-hexyl) carbonate by transesterification reaction of an alkyl carbonate with 2-ethyl-1-hexanol. The preferred reaction temperature is from about 200° to 400° F. Since DMC and DEC boil at temperatures higher than about 305° F., creating a vapor phase in large commercial fixed bed reactor becomes difficult at relatively high liquid flow rates. By controlling the flow of vapor volume to the reactor at a given flow rate of liquid reaction mixture in a dual phase reactor as disclosed in this invention, it becomes relatively easy to create the proper volume of gas phase in the reaction zone at given reaction conditions and maintaining a steady state reactor operation. Significant advantages obtained over prior art are:

(a) high productivity of desired products, (b) high selectivity of desired products, (c) no separation of catalyst from the reaction product stream, (d) excellent catalyst life, (e) less energy consumption and (f) easy regeneration of deactivated catalyst.

The feed to transesterification reactor preferably comprises fresh phenol and DEC, and a mixed recycle stream containing DEC, PhOH and EPC. An essentially ethanol-free feed stream to transesterification reactor creates favorable conditions for the conversion of phenol and a high reaction rate. This is also true for essentially DEC-free feed stream to disproportionation reactor. There are practically no cold spots in the catalytic reaction zones, which is important for maintaining steady reaction rates. Since there are both vapor and liquid phases in transesterification and disproportionation reaction zones in dual phase reactors, light reaction products (ethanol and DEC in each reaction zone) are vaporized to a gas phase which creates favorable conditions for high productivity of the intended products. As there is no exposure of reactants or products to unnecessarily high temperature in the presence of catalyst, there are less undesired by-products, which makes it easier and cheaper to purify crude DPC product stream. Because the feed stream to disproportionation reaction zone may be composed of fairly high boiling compounds, such as EPC or MPC, nitrogen, a low boiling component or both are introduced into the reaction zone to create sufficient volume of gas phase in the reaction zone. Examples such low boiling components are ethyl ether, propyl ether, dimethyl ether, methane, ethane, propane, butane, hexane, heptanes, toluene, and xylenes.

Preferably all or at least substantial portion of low boiling components are introduced into the reaction zone as super heated gas. Since ethanol and DEC do not form an azeotrope, DEC separation for recycle results in lower energy consumption and lower construction cost compared with existing commercial processes where DPC is produced from DMC and phenol.

There are two or three reaction zones. In the first reaction zone, an alkyl aryl carbonate such as EPC is produced by transesterification of DEC with phenol. In the second reaction zone, DPC is produced by performing disproportionation of EPC. The reaction zones comprise two fixed bed reactors. Optionally three reaction zones may comprise three fixed bed reactors or two fixed bed reactors and a catalytic distillation column reactor. The reactors are loaded with one or two different heterogeneous catalysts.

Examples of organic carbonates produced by this invention are DPC, EPC, MPC, DEC, DMC, bis-(2-ethylhexyl) carbonate, and fatty acid mono-glyceride carbonates. The present invention is particularly useful in producing diphenyl carbonate (DPC) from DEC and phenol. Although DEC is the preferred dialkyl carbonate for the production of DPC, it is understood that the process is also useful for the production of DPC by using DMC or any other alkyl carbonate or alkyl aryl carbonate.

To avoid excessive heating of the reboiler while conducting transesterification and disproportionation in catalytic distillation column reactor, a low boiling component or a mixture of low boiling components may be pumped directly into the reboiler. Therefore, this technique is a part of the present invention for production of various organic carbonates for both solid catalysts and homogeneous catalyst used in a process. This technique has not been disclosed in the prior art for the production of organic carbonates such as DPC, DEM, and DEC.

The preferred heterogeneous catalysts are supported mixed oxides, hydroxides, oxyhydroxides and alkoxides of Group IV, V and VI elements which are deposited on porous supports. The mixed oxide catalysts may be combinations of two, three or four elements chosen from Mo, Nb, Ti, V Zr, Bi, and Si. These element are deposited in oxide or hydroxide or oxyhydroxide forms on a porous support such as silica, zirconia, and titania. Supports can be pellets, granules, extrudates, spheres, and the like in sizes of from about 1 to about 5 mm. The deposition can be carried out in a single step or multiple steps. The examples of the mixed oxide catalysts are $Nb_2O3$—$TiO_2$, $V2O_3$—$TiO_2$, $MoO_3$—$TiO_2$, $TiO_2$—$ZrO_2$, $Nb_2O_5$—$V2O_3$, $MoO_3$—$V_2O_5$, $MoO_3$—$ZrO_2$, $TiO_2$—$ZrO_2$—$SiO_2$, $TiO_2$—$Nb_2O_5$—$SiO_2$, $MoO_3$—$Nb$ $O_5$—$TiO_2$, $V_2O_5$—$Nb_2O_5$—$TiO_2$, $MoO_3$—$Nb_2O_5$—$SiO_2$, $TiO_2$—$Bi_2O_3$—$SiO$ , $MoO_3$—$NbO_5$—$ZrO_2$, $TiO_2$—$Nb_2O_5$—$Bi_2O3$, $MoO_3$—$V_2Os$—$TiO_2$, $TiO_2$—$Bi_2O_3$—$SiO_2$, $MoO_3$—$Bi_2O_3$—$SiO_2$, $TiO_2$—$ZrO_2$—$Bi_2O_3$—$SiO_2$, and $TiO_2$—$ZrO_2$—$Nb_2O_5$—$Bi_2O_3$—$SiO_2$.

The general procedure for preparing these mixed oxide catalysts are impregnation and co-precipitation or a combination of these two, which are performed in a single step or multiple steps. One may perform impregnation of one, two or three metal components on a porous support or on a mixed oxide support prepared by co-precipitation. Impregnation can be performed in one step or multiple steps.

Co-precipitation products and impregnation products obtained in powdery forms are subjected to suitable heat treatment at temperatures from about 150° to about 600° C. The powdery materials are shaped in a suitable size of from about 1 to 5 mm for the fixed bed reactor. The shaped materials are calcined at temperature from 200° to about 750° C., preferably from about 250° to about 600° C. in air. Optionally one or two metal components can be deposited on a shaped material prepared by a co-precipitation or impregnation method in either powder form or shaped form and then calcined at from 200° to about 750° C., preferably from about 250° to about 600° C. in air. The co-precipitation and impregnation can be carried out in aqueous phase or in organic phase, such as hydrocarbons, ethers, ketones, alcohols, and mixtures of these.

When precipitation is carried out in organic phase, organometallic compounds are preferably used. For example, two different solutions of different organometallic compounds are added to a suitable organic solvent simultaneously with vigorous stirring under precipitation conditions at suitable temperatures. Sometimes a third solution is necessary during the addition or afterward to cause gelation or precipitation. An example of the third solution is water, basic or acidic water solution in a suitable organic solvent such as alcohol, ether, ketone, organic ester, or mixtures of these. Another optional method is simultaneously adding first organometallic solution and third solution to second organometallic solution with vigorous stirring. If necessary, the precipitates are aged at a suitable temperature form about 25° to about 200° C. for from 30 minutes to about 30 hours in suitable medium. Sometimes a coprecipitated product in aqueous medium is aged in neutral, mildly acidic or basic organic medium.

The aging medium may or may not contain a minor amount of water depending on the nature of the material to be aged. The aging medium could be mildly acidic, mildly basic or neutral. The aged product is dried at a temperature from about 100° to about 400° C. and then calcined at a temperature from about 250° to about 750° C. If necessary, impregnation of one or two elements on a suitable support is carried out by using an organic solution containing one or two organometallic compounds or aqueous solution containing one or two compounds. Optionally one can perform multiple impregnations by using different solutions.

However, one may choose to use any heterogeneous catalyst disclosed in the prior art, as long as the catalyst is suitable for a fixed bed reactor for the operation of a large commercial reactor. Examples of heterogenous catalysts disclosed in the prior art are titanium oxide, TS-1, Ti-MCM-41, molybdenum oxide, vanadium oxide, niobium oxide, lead oxide, and MgLa mixed oxide as appropriate and preferably supported as described herein.

It is important that a support should have surface hydroxyl groups. Silica is a preferred support. The term "treated support" or "treated silica" is understood to mean a support having an optimized population of surface hydroxyl groups for a given surface area for the preparation of the catalysts described herein. Depending on how silica is prepared, silica may not have a sufficient number of surface hydroxyl groups in a given surface area. For such a silica, the silica is treated to introduce extra surface hydroxyl groups with an aqueous base solution and then washed thoroughly with water, followed by calcination at a temperature from 280° to 650° C., prior to use. Optionally one may attempt to rehydrate a commercially available silica support. The rehydrated silica is calcined at a temperature from 280° to 650° C. to optimize the population density of surface hydroxyl groups prior to use. Therefore, the preferred silica support used for the preparation of a solid catalyst is "treated silica". A class of preferred supports, particularly silica supports are those that have had the surface hydroxyl groups increased by treatment with a base solution as describe to obtain the maximum number of hydroxyl groups without degrading the physical integrity and strength of the support. Controlling the sodium content on silica support is very important for the preparation of aromatic carbonates such as EPC and DPC, because basic impurities such as alkali metal oxide on silica causes unwanted side reactions and tends to cause catalyst instability. Alkali metal on silica support causes instability of the catalyst performance and undesired side reactions for the transesterification and disproportionation, which produces alkyl aryl carbonate and diary carbonate. The preferred "treated silica" support will have less than about 0.05 wt % Na, preferably less than about 0.03 wt % Na. Treating silica with aqueous alkali metal solution has an additional benefit of widening the pores. However, leaching out too much silica from silica support during the treatment with alkali metal solution can cause the problem of maintaining physical integrity and strength.

Other catalysts disclosed in this invention are supported metal alkoxide or mixed metal alkoxide catalysts, which are prepared by bonding metal alkoxides to porous supporting materials through oxygen bridge bonds. The porous supporting materials must have surface hydroxyl groups, which react with alkoxy groups for the formation of oxygen bridge bonds. The preferred support is treated silica, which has less than about 0.05 wt % Na, preferably less than about 0.03 wt % Na. Optimizing the population of the surface hydroxyl groups on silica support is very important to create stable, strongly anchored metal alkoxide active sites, since no high temperature calcinations is involved to link active metal atoms to the surface of silica via M—O—Si bridge bonds. Maximizing the number of M—O—Si bridge bonds is highly desirable.

Thus, an optimized population of hydroxyl groups for a given surface includes the maximum number of hydroxy groups that can be obtained for the given surface area within the constraints of alkali metal content and support strength as described above.

The preferred metal alkoxides are Group IV and V metal alkoxides such as titanium alkoxides, zirconium alkoxides, vanadium alkoxides, niobium alkoxides, and the like. The Group V metal alkoxides include a lower valent alkoxide such as tetra-alkoxide and an oxytrialkoxide such as $VO(OR)_3$ or oligomers of oxoalkoxide. Examples of preferred supports are silica, zirconia, titania, titania-silica, silica-alumina, and silica-zirconia. Using treated silica is especially important for the preparation of supported metal alkoxide catalysts. An alkoxide catalyst on a support can have one or two different metal alkoxides.

The heterogeneous metal alkoxide catalysts are prepared by contacting a metal alkoxide solution or a mixed solution of two different metal alkoxides with a support such as silica at temperature from about 20° to about 400° F., preferably from about 40° to about 300° F. The alkoxide solution is prepared by dissolving one or two different metal alkoxides in a solvent. The solvent must not interfere with the oxygen bridge forming reaction in any way. Examples of such solvents are hydrocarbons, ethers, ketones, alcohols and mixtures thereof. When two different metal alkoxides are supported on a support, optionally two different metal alkoxide solutions are prepared and are reacted with a support in sequence.

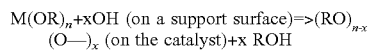

Where n=4 or 5, x=1, 2, 3 or 4 and R=alkyl or aryl group

Supported titanium alkoxide is an acidic catalyst. The higher activity of supported titanium alkoxide catalyst on silica compared to titanium alkoxide in homogeneous catalyst is attributed to higher acidity of the supported $Ti^{+4}$. The catalyst acidity plays an important role for acid catalyzed transesterification and disproportionation reactions in producing aromatic carbonates.

It is possible to prepare a supported metal alkoxide catalyst insitu as an optional method. Reactors are loaded with a treated support. Metal alkoxide solutions are circulated through the reactor at a temperature from ambient to about 400° F. After formation of a supported metal alkoxide catalyst, any remaining solvent is drained off from reactors. After washing the reactors with a suitable solvent such as ethanol, pentane, or toluene and optionally heat treatment of the catalysts in flow of an inert gas such as nitrogen at a temperature from about 80° to about 400° F., preferably from about 100° to about 350° F., the catalysts are ready for the transesterification and disproportionation. For the preparation of supported metal or mixed metal alkoxide catalysts, it is especially important to use a "treated support". An example of a treated support is the treated silica described above.

In the present invention deactivation of heterogeneous catalysts was observed. This is especially true for the disproportionation reaction of alkyl aryl carbonates such as MPC., EPC., etc. It was observed that the cause of catalyst deactivation is the deposition of heavy polymers on solid catalyst, which blocks the catalyst active sites and fills up the catalyst pores. The deactivated catalyst is either dark brown or black, depending on the degree of polymer deposition. The deactivation rate for a given heterogeneous catalyst is much faster for a disproportionation reaction than a transesterification reaction. It was discovered that deactivated catalyst could be regenerated insitu by depolymerizing the polymers deposited on the catalyst by contacting the deactivated catalyst with a compound containing a hydroxyl group, such as steam, methanol, ethanol, phenol, or mixtures of hydroxy compounds at an elevated temperature. Optionally one can use a solution of hydroxy compound in a solvent. The preferred solvents are benzene, toluene, xylenes, pentane, hexane, octane, decane, THF or any mixtures of solvents. The use of a solvent for the depolymerization of polymers deposited on deactivated catalyst is only optional and not required. The regenerated catalyst is preferably dried at temperature from 200° to about 500° F. in an inert gas (e.g. nitrogen) flow prior to use. The catalyst regeneration with hydroxy containing compounds was performed by treating deactivated catalysts insitu in the flow of an alcohol or water-alcohol solution or with steam at a temperature from 250° to 600° F., preferentially from 270° to 450° F. The treatment of the deactivated catalysts may be performed with both alcoholic solution and steam. For example, a deactivated catalyst may be treated first with alcohol or alcohol solution and then with steam or in reverse order. It is preferable to perform the catalyst regeneration under sufficient pressure so that at least, some liquid phase present in the catalyst bed. The preferred alcohol is methanol, ethanol or mixture of these two. Optionally an alcohol solution may contain water in amount of up to 80 wt %, preferably up to 20 wt %, most preferably up to 5%. The stream from the depolymerization reactor contains phenol, DEC, EPC and trace amounts of phenetole and heavies as depolymerization reaction products.

To use a glycol ether to wash off the polymers on the catalyst and improve selectivity, the solvent as described above, is introduced as a component of reaction mixture to a catalytic reaction zone and separated from reaction mixture for recycling. The examples of such ether solvents are ethylene glycol diethyl ether, ethylene glycol dimethyl ether, diethylene glycol diethyl ether, diethylene glycol dimethyl ether, etc.

The catalyst regeneration technique disclosed in this invention can also be used in any process for the production of aromatic carbonates, where a homogeneous catalyst is used. For the regeneration of a homogeneous catalyst system, an alcohol solution must be fairly dry so that water content may not exceed about 0.2 wt %. Therefore, the catalyst regeneration technique disclosed in this invention is applicable for any process for producing organic carbonates.

It was surprisingly discovered that this catalyst deactivation could be alleviated by performing the disproportionation reaction in the presence of an aromatic hydroxy compound such as phenol. Furthermore, there is an additional benefit by the performing disproportionation in the presence of a trace amount of water in the catalytic reaction zone in an amount of up to 0.3 wt %, preferably up to 0.10%. It appears that the substantial portion of heavy polymers deposited on the catalysts are polycarbonates. Performing disproportionation in the presence of an aromatic hydroxyl compound or both aromatic hydroxyl compound and a trace amount of water in the catalytic reaction zone results in acceptable stable catalyst performance. However, it is understood that too much of an aromatic hydroxy compound results in unacceptably low rate of producing DPC due to the equilibrium nature of the transesterification reaction. Therefore, maintaining the mole ratio of aromatic hydroxy compound to DPC from 0.05 to 10, preferably from 0.1 to 6, in the disproportionation reaction zone is essential to ensure both long acceptable catalyst cycle time and good productivity of DPC. For the transesterification reaction, the mole ratio of phenol to DEC is maintained higher than 0.2, preferably higher than about 0.3, most preferably higher than about 0.35.

An example of the schematic process flow diagram for the production of DPC is illustrated in the figure. There are two fixed bed, dual phase reactors and five distillation columns. The first dual phase reactor 38 is primarily for the transesterification reaction to produce EPC from DEC and phenol. The second dual phase reactor 37 is primarily for the disproportionation reaction to produce DPC from EPC. Both dual phase reactors 38 and 37 are loaded with either a heterogeneous catalyst or optionally two different heterogeneous catalysts disclosed in this invention. Optionally one may introduce additional fixed bed reactors (not shown) in series between 38 and 37. The major objective of this additional reactor is to produce additional EPC. The fresh phenol feed stream 1 and fresh DEC feed stream 2 are mixed with recycle streams 11 and 25, and then introduced to the dual phase reactor 38 through line 3. Optionally a nitrogen gas stream is introduced to 38 via line 4. The product EPC and the co-product ethanol are produced by performing the transesterification in 38. In the reactor 38, the co-product ethanol is vaporized into gas phase. The reactor effluent stream 5 is introduced to the first distillation column 30 via lines 5, 6 and 7. Ethanol is stripped off in the column 30 to overhead stream 8 with small amount of DEC. Stream 8 is partially cooled and then introduced to gas-liquid separation drum 36, and the gas stream 9 is recycled to the Reactor 38 and 37. The liquid stream 10 (ethanol) from 36 is recycled to DEC plant to produce DEC. A side-draw stream 11 from column 30, which is composed of DEC, phenol and EPC is recycled back to the reactor 38 through line 3. Optionally one may choose to place a catalyst bed 101 at the bottom section of the column 30 below the sidedraw point for the additional conversion of phenol to EPC. The distillation column 30 is designed and operated so that the side-draw stream 11 is essentially free of ethanol. The recycle loop for the dual phase reactor 38 comprises the lines 5, 6 and 7, column 30, and lines 11 and 3. The bottom stream 12 from the column 30 is introduced to the second dual phase reactor 37 via lines 13 and 14. The stream 12 contains EPC and phenol. But it also contains small amounts of DPC and the by-product phenetole. The column 30 is also designed and operated to minimize the DEC in the bottom stream 12. The stream 12 is combined with recycle stream 19 to stream 13. The stream 13 is combined with nitrogen gas stream 15 to the stream 14, which is introduced to 37. The product DPC and the co-product DEC are produced in the reactor 37 by performing disproportionation of EPC. DEC in the reactor 37 is vaporized to gas phase. The reactor effluent steam 16 is introduced to the second distillation column 32. The stream 16 is composed of mostly DEC, EPC, phenol, DPC, and small amounts of ethanol and by-products. Ethanol and DEC in stream 16 are stripped off along with vapor in the column 32 as overhead stream 17, which is introduced to the first column 30 via line 7. The bottom stream 18 from the column 32 splits to two streams 19 and 20. The stream 19 is recycled back to the second reactor 37 via lines 13 and 14. The recycle loop for the second dual phase reactor 37 comprises the line 16, column 32, and lines 18, 19, 13 and 14. The other stream 20 is introduced to the third distillation column 34, where remaining DEC in the stream is recovered as overhead stream 21, which is sent to the first column 30 via the lines 6 and 7. A side-draw stream 22 from 34 is introduced to the fourth distillation column 35 to remove the byproduct phenetole as the overhead stream 24. The bottom stream 25 from the column 35 is recycled to 38. Optionally the bottom stream 25 from 35 may be recycled to the first column 30 via lines 31, 21, 5, 6, and 7. The bottom stream 23 from 34 is introduced to distillation column 33 to recover the product DPC. The overhead stream 26, which is mainly composed of EPC, is recycled to the disproportionation reactor 37 via line 14. The column 33 is operated under sub-atmospheric pressure. The bottom stream 27 from 33 is the crude DPC stream. One may choose to use other material, such diethyl ether, dimethyl ether, isopentane or butane, in place of nitrogen gas or to partially replace the nitrogen gas for the operation of the two dual phase reactors, 38 and 37.

CONTROL EXAMPLE 1

A titanium oxide (9.2 wt %) catalyst supported on silica was prepared according to the prior art (WO 03/066569). 3.839 Ti(OC$_4$ Hg-n)$_4$ was dissolved in 90 ml dry toluene. Granular silica (+8 mesh, 655 ppm Na by weight, 300 m2/g BET SA and 1 cc/g PV) was pre-dried at 330° C. for 2 hrs in air. The titanium butoxide solution was refluxed with 25 ml (9.159) of the dried silica granules in boiling toluene solution in a 200 ml flask with a condenser. After about 6 hours reflux, the excess toluene in the flask was boiled off from the flask. The titanium butoxide supported silica was recovered from the flask and dried at 120° C. in a vacuum oven for 1.5 hours. The dried silica was calcined at 500° C. for to 2 hours. The calcined product was paper white granule. The total catalyst weight was 9.67 g. This is catalyst A.

EXAMPLE 2

A mixed niobium/titanium oxide catalyst supported on silica was prepared according to the invention. 0.592 g of Nb(OC$_4$H$_{9-n}$)$_5$ was dissolved in 80 ml toluene. The granular silica used in the Control Example 1 is dried at 320° C. for 2 hours in air. 25 ml (9.27g) of this dried silica is refluxed with the above niobium butoxide solution. After 5.5 hours reflux in the same fashion as the Control Example 1, the excess toluene was drained out from the flask. A water solution in methanol prepared by mixing 0.209 g of water with 120 ml methanol was poured into flask and then the solution was refluxed in boiling methanol for an hour. The excess of methanol was drained out from the flask. A titanium tetrabutoxide solution prepared by dissolving 3.56 g of titanium butoxide in 90 ml toluene was poured into the flask and then the content in the flask was refluxed in boiling toluene for 5.5 hours. The excess toluene in the flask was boiled off from the flask. The material in the flask was recovered from the flask and dried at 120° C. in a vacuum oven for 1.5 hours. The dried silica was calcined at 500° C. for to 2 hours. The appearance of the calcined product was different from the catalyst in the Control Example 1. It looked more like granular silica support than the paper white catalyst in the Control Example 1. The total catalyst weight was 10.28 g. This is catalyst B.

EXAMPLE 3

In this example, treated silica was used to prepare a mixed titanium/niobium oxide catalyst supported on silica. A mixed niobium/titanium oxide catalyst supported on treated silica was prepared according to the invention. The same granular silica of Control Example 1 was used to prepare the treated silica of this example. The granular silica(40.56 g) was treated with a sodium hydroxide solution prepared by dissolving 8.059 NaOH in 226 g water at room temperature for 7 minutes with stirring. The treated silica was washed with cold water thoroughly and then with hot water (about 65° C.) several times to remove trace of sodium on silica. The treated silica was dried at 150° C. for 2 hours and then calcined at 325° C. for 2 hours. This calcined silica contained 300 ppm Na by weight. A niobium alkoxide solution was prepared by dissolving 0.844 g of $Nb(OC_4H_{9-n})_5$ in 80 ml toluene. 8.46 g of the treated silica was refluxed in the above niobium butoxide solution for 3 hours in a flask with water-cooled condenser. After cooling, the excess solution in the flask was drained out of the flask. A water-methanol mixture was prepared by mixing 0.645 g water with 90 ml methanol. This water-methanol mixture was poured into the flask and the content in the flask was again refluxed. After an hour reflux, the excess solution in the flask was drained out. A titanium tetrabutoxide solution prepared by dissolving 3.67g of titanium butoxide in 80 ml toluene was poured into the flask and then the content in the flask was refluxed for 1 hour 45 minutes. The excess toluene in the flask was distilled off from the flask. The material in the flask was recovered from the flask and dried at 120° C. in a vacuum oven for 1 hour. The dried silica was calcined at 500° C. for to 2 hours. The appearance of the catalyst was more like granular silica support. This is catalyst C.

EXAMPLE 4

A titanium alkoxide catalyst supported on treated silica was prepared according to the invention. The same granular silica (80.55 g) used in the Control Example 1 was treated with a sodium hydroxide solution prepared by dissolving 8.3 g NaOH in 580 ml of deionized water at room temperature for 8 minutes with stirring. The treated silica was washed with cold water and then hot water. The washed silica was treated with ammonium nitrate solution prepared by dissolving 99 g ammonium nitrate in 2 liter deionized water at 80° C. for 2 hours. The treatment of silica with ammonium nitrate solution was repeated 13 times. Finally the silica washed with deionized water at ambient temperature. The washed silica was dried at 110° C. for an hour, followed by calcination at 370 for 1.5 hours and then 375° C. for 30 min. The calcined silica contained 23 ppm Na by weight and 2.9 wt % weight loss on calcinations at 550° C. A titanium tetrabutoxide was prepared by dissolving 4.74 g titanium tetrabutoxide in 70 ml toluene. 10.44 g (31 ml) of treated silica was refluxed in the titanium tetrabutoxide solution with for 6 hours and then the excess titanium solution in the flask was drained out. The drained titanium solution contained 0.50 wt % Ti. The silica was washed with 90 ml toluene at room temperature. The washed product was dried at 170° C. for 3 hours in a vacuum oven. The appearance of the finished catalyst looked like treated silica granules. A small portion of this finished catalyst was calcined at 500° C. for 2 hrs in air to determine Ti content on the catalyst. The Ti content of the calcined catalyst is 3.25%. The appearance of the calcined catalyst looked like treated silica granules. This experiment indicates a successful support of titanium alkoxide on treated silica.

Performing Transesterification and Disproportionation

The catalysts were tested in a unit having a fixed bed reactor, a distillation column and a reflux drum. The dimension of the fixed bed reactor was ½ inches diameter and 15 inches long. It had three thermocouples to monitor temperatures at three positions just above the catalyst bed, the middle of catalyst bed, and just below the catalyst bed. The top half and bottom half of the reactor temperatures are independently controlled. The unit also had a feed preheater at the top of the fixed catalyst bed, whose temperature is separately controlled. The fixed bed reactor was operated in down flow mode. The distillation column consists of a 2 liters capacity reboiler and 42"×1" OD (0.870" ID) column. There were three pressure transmitters to control and record the column overhead pressure, the top and bottom of the catalyst bed. Also the reboiler had a liquid level transmitter. The fixed bed had a recirculation loop; the stream to the reactor from the liquid medium in the reboiler was pumped through the reactor in down flow and then returned to the reboiler. The fresh feed DEC was pumped into the recirculation loop prior to the reactor. The fresh phenol feed solution was separately pumped into the recirculation loop prior to the reactor. Nitrogen gas was introduced into the system as necessary. The vapor from the distillation column was condensed and removed as an overhead liquid stream. Uncondensable gas was discharged from the condenser.

For the continuous run for the transesterification, the phenol feed solution was continuously fed at a given rate, while continuously removing product stream from the reboiler at a predetermined constant rate and continuously removing overhead product. The DEC feed rate is a cascade to maintain a constant liquid level in the reboiler.

Test 1

The purpose of this run is to demonstrate the performance of a dual phase fixed bed reactor for the transesterification reaction. The dual phase in the catalytic reaction zone was created by a boiling mixture of vapor phase and liquid phase in the catalytic reaction zone.

The catalyst A (25 ml; 9.67 g) was loaded in the reactor. 167.6 g phenol and 737.4 g DEC were charged in the reboiler.

The testing was performed at the following conditions:
  The overhead column press: 18 psig
  Reboiler temperature: 335° F.
  Distillation column temperature: 300-310° F.
  Recirculation rate: 66 ml/min
  Pressure at top of fixed bed reactor: 24.6 psig
  Pressure at btm of fixed bed reactor: 20.5 psig
  Fixed bed reactor temperature: 338-342° F.
  Nitrogen flow rate to the reboiler: 60 ml/min
  0 reflux from reflux drum
  Run hours started when the fixed bed reactor temperature reached the target temperature of 340° F. During the run, DEC was continuously pumped in to maintain a constant liquid level. After running for 45 hours, 23 g phenol was charged into the system as a 20.92 wt % phenol solution over a period of 55 minutes at 2 ml/min flow rate. The run was continued to 77 hours on stream time. The average overhead liquid flow rate was about 0.3 ml/min. The overhead stream was composed mainly of DEC and a small amount of ethanol. Samples were taken from the reboiler and overhead stream for analysis. At the end of 77 hours run time, 64.8 mole % of phenol charged to the unit had been converted. The yields were 63.1 mole % EPC; 1.52 mole % DPC and 0.26 mole % by-products based on the total amount of phenol charged into the system. Phenetole was the major by-product, which accounted for 33.6 mole % of byproducts. The average productivity was 1.81 m/h/kg of catalyst for EPC; 0.041 m/h/kg of catalyst for DPC and 0.01 m/h/kg of catalyst for by-products. The productivity of EPC in this example is superior to those disclosed in prior art, demonstrating the superior productivity of the process disclosed in this invention.

Test 2

The purpose of this run is to demonstrate the performance of a dual phase fixed bed reactor and a mixed niobium and titanium oxide catalyst according to the invention for the transesterification reaction. The dual phase in the catalytic reaction zone was created by a boiling mixture of vapor phase and liquid phase in the catalytic reaction zone.

Catalyst B (24 ml; 9.172 g) was loaded in the reactor. This test was performed under the identical condition to Test 1. 167.6 g phenol and 737.4 g DEC were charged in the reboiler. Run hours started when the fixed bed reactor temperature reached the target temperature of 340° F. During the run, DEC was continuously pumped in to maintain a constant liquid level. After running for 22 hours, 91.62 g phenol was charged into the system as 31.38 wt % phenol solution over a period of 2 hours 20 minutes at 2 ml/min flow rate. The run was continued to 73 hours on stream time. The average overhead liquid flow rate was about 0.3 ml/min. The overhead stream was composed mainly of DEC and a small amount of ethanol. Samples were taken from the reboiler and overhead stream for analysis. At the end of 73 hours run, 64.6 mole % of phenol charged to the unit had been converted. The yields were 63.1 mole % EPC; 1.4 mole % DPC; and 0.27 mole % by-products based on the total amount of phenol charged into the system. Phenetole was the major by-product, which was accounted for 55.9 mole % of by-products. The average productivity was 2.567 m/h/kg of catalyst for EPC; 0.059 m/h/kg of catalyst for DPC and 0.022 m/h/kg of catalyst for by-products. The major by-product was phenetole, which was accounted for 33.6 mole % of the total by-products. The productivity of EPC in this example is superior to the catalyst disclosed in prior art and Test 1.

Test 3

This test was performed to demonstrate the disproportionation of EPC to DPC in batch operation. The fixed bed reactor was operated in boiling point mode by using the same equipment as described.

A crude feed was prepared as in the Test 2 and then the excess of DEC in the crude feed was distilled off to concentrate EPC and then toluene was added to it. The purpose of toluene addition to the concentrated crude feed was to perform the disproportionation under the dual phase mode in the down flow reactor. Boiling reaction mixture of vapor phase and liquid phase were created in the reaction zone. Run hours started when the fixed bed reactor temperature reached the target temperature of 340° F. The test was performed with the same catalyst used in the Test 2. During the run, toluene was continuously pumped in to maintain a constant liquid level and the overhead flow rate was about 7 ml/min. The overhead stream was composed mainly of toluene, a small amount of DEC and a trace amount of ethanol. The total weight of the feed in the reboiler was 635.3 g. The composition of the feed was 44.19 wt % toluene; 8.42 wt % DEC; 0.07 wt % phenetole; 0.29 wt % by-products; 11.21 wt % phenol; 31.88 wt % EPC and 3.94 wt % DPC. The testing was performed at the following conditions:

The overhead column press: 16.3 psig
Reboiler temperature: 311° F.
Distillation column temperature: 295-305° F.
Recirculation rate: 67 ml/min
Pressure at top of fixed bed reactor: 32.8 psig
Pressure at btm of fixed bed reactor: 18.5 psig
Fixed bed reactor temperature: 327-330° F.
Nitrogen flow rate to the reboiler: 50 ml/min
0 reflux from reflux drum After 6 hours operation, the analysis of product from reboiler indicated 5.8 mole % conversion of EPC with 95.2 mole % selectivity to DPC. The productivity of DPC was 0.614 m/h/kg of catalyst.

Test 4

This test was performed to demonstrate a continuous run for the production of EPC with a fixed bed reactor operated in boiling point reactor mode under a steady state condition.

Another batch of the catalyst identical to the catalyst B in the Example 2 was prepared. 9.04 g (about 25 ml) of this catalyst was loaded in the reactor. 200 g phenol and 610 g DEC were charged in the reboiler for a continuous run. Run hours started when the fixed bed reactor temperature reached the target temperature of 340° F. During the run, DEC was continuously pumped in to maintain a constant liquid level. After running for 23.25 hours, 85.58 g phenol was charged into the system as 31.38 wt % phenol solution over a period of 2 hours 15 minutes at 2 ml/min flow rate. The continuous run at a steady state condition was performed by continuously pumping in 32.2 wt % phenol solution in DEC at 0.18 ml/min and continuously removing the product stream at 0.15 ml/min. DEC was pumped in to maintain a constant liquid level 81% in reboiler. At 242.5 hrs on stream time under at steady state operation condition, the following result was obtained:

| | |
|---|---|
| On stream time: | 242.5 hrs |
| The overhead column press: | 19.6 psig |
| Reboiler temperature: | 354° F. |
| Distillation column temperature: | 330° F. |
| Recirculation rate: | 67 ml/min |
| Pressure at top of fixed bed reactor: | 20.8 psig |
| Pressure at btm of fixed bed reactor: | 19.2 psig |
| Fixed bed reactor temperature: | 341° F. |
| Nitrogen flow rate to the reboiler: | 60 ml/min |
| Reflux from reflux drum: | 0 |
| Liquid level in reboiler: | 81.04% |
| Feed rate of 32.2 wt % PhOH/DEC solution: | 0.15 ml/min |
| DEC flow rate: | 0.28 ml/min |
| Ovhd flow rate: | 0.269 ml/min |
| BTM product flow rate: | 0.185 ml/min |

| Composition of Streams (wt %): | | |
|---|---|---|
| COMPONENT | OVHD | BTM |

-continued

| Ethanol | 3.5793 | 0.0448 |
| DEC | 96.1344 | 62.5443 |
| Phenetole | — | 0.0176 |
| Phenol | 0.2208 | 17.5226 |
| EPC | 0.0655 | 19.2401 |
| DPC | — | 0.6306 |

Phenol Conversion (mole %) 39.5   EPC selectivity: 95.04 mole %
EPC Yield: 37.6 mole %   DPC Selectivity: 4.87 mole %
DPC Yield: 1.9 mole %   Phenetole Selectivity: 0.05%
EPC Productivity: 1.50 m/h/kg catalyst Phenetole was the only by-product detected in the product stream by gc and gc-ms. This is a result superior to prior art. Deactivation of the catalyst was observed.

Test 5

This test was performed to demonstrate a continuous run for the transesterification reaction between propylene carbonate and ethanol to produce DEC and propylene glycol coproducts by using a fixed bed reactoroperated in boiling point mode.

Another batch of the catalyst identical to the catalyst B in the example 2 was prepared. 9.6 g (about 25 ml) of this catalyst was loaded in the reactor. 280 g propylene carbonate and 635 g ethanol were charged in the reboiler for a continuous run. Run hours was started when the fixed bed reactor temperature reached the target temperature of 335° F. During the run, the product stream was continuously removed from the reboiler at a constant rate of 0.14 ml/min. To maintain a constant liquid level of 85%, a 23.1 wt % propylene carbonate solution in ethanol was continuously pumped in to the reactor cascade mode. The run was continued for 162 hours. During the run, the conversion of propylene carbonate was fairly constant. The average conversion of propylene during the run was 14.5 mole %. The average DEC productivity was 1.81 mole/h/kg of catalyst.

Test 6

The objective of this experiment is to demonstrate a superior performance of the mixed oxide catalyst supported on treated silica to the conventional catalyst disclosed in prior art. A slower deactivation rate, higher activity of the Catalyst C and the catalyst regeneration by depolymerization of deactivated Catalyst C were demonstrated. The test of a conventional titanium oxide catalyst supported on silica (The Control Example 1) was performed in Test 6A. The test of the mixed Ti/Nb oxide catalyst supported on treated silica (Catalyst C in the Example 3) was performed in the Test 6B.

Test 6A

Another Ti oxide catalyst similar to the Catalyst A in the Control Example 1 was prepared. The only difference from the Control Example 1 was the calcination of the same silica at 340° C. for 4 hours in air. 25 ml (9.0 g) catalyst was loaded in the was prepared. The only difference from the Control Example 1 was the calcination of the same silica at 340° C. for 4 hours in air. 25 ml (9.0 g) catalyst was loaded in the fixed bed reactor described. The appearance of this catalyst is white sugar coated silica granules the same as the catalyst of the Control Example 1. 285 g phenol and 530 g DEC were charged in the reboiler. The testing was performed at the following conditions:

The overhead column press: 19-21 psig
Reboiler temperature: 345-347° F.
Distillation column temperature: 270-285° F.
Recirculation rate: 66-67 ml/min
Pressure at top of fixed bed reactor: 20-22 psig
Pressure at btm of fixed bed reactor: 19-22 psig
Fixed bed reactor temperature: 332-337° F.
Nitrogen flow rate to the reboiler: 60 ml/min
0 reflux from reflux drum
PhOH/DEC solution flow rate: 0.17-0.18 ml/min
Btm flow rate: 0.18-0.19 ml/min During the run, the flow of DEC was cascaded to a liquid level of 88% (arbitrary scale) in to maintain a constant liquid level. The run was performed by continuously draining the reaction mixture in the reboiler, while pumping in 40.4 wt. % phenol solution in DEC at a constant rate of about 0.19 ml/mint The run was continued for 115 hours without interruption. The overhead stream was composed of mostly DEC., ethanol and small amounts of phenol and EPC. Samples were taken from the reboiler and overhead stream for analysis. Phenetole was the only by-product in the bottom product stream from the reboiler. The results are listed in Table 1.

TABLE 1

| | Hours on stream time | | | |
| --- | --- | --- | --- | --- |
| | 31 | 61 | 85 | 115 |
| Phenol conversion (m %) | 17.8 | 20.8 | 17.7 | 11.9 |
| EPC productivity (m/h/kg) | 0.771 | 0.869 | 0.754 | 0.502 |
| DPC productivity (m~/kg) | 0.008 | 0.013 | 0.013 | 0.0092 |
| Phenetole productivity (m/h/kg) | .0016 | 0.0018 | 0.0018 | 0.0017 |

Test 6B

The performance of the Catalyst C prepared in the Example 3 was tested for the transesterification of DEC with phenol. 8.4 g (25 ml) catalyst C was loaded in the fixed bed reactor. 287 g phenol and 530 g DEC were charged in the reboiler. The testing was performed at the following conditions:

The overhead column press: 17-19 psig
Reboiler temperature: 345-348° F.
Distillation column temperature: 270-285° F.
Recirculation rate: 66-67 ml/min
Pressure at top of fixed bed reactor: 19-21 psig
Pressure at btm of fixed bed reactor: 19-22 psig
Fixed bed reactor temperature: 331-335° F.
Nitrogen flow rate to the reboiler: 60 ml/min
0 reflux from reflux drum
PhOH/DEC solution flow rate: 0.18-0.19 ml/min
Btm flow rate: 0.18-0.20 ml/min During the run, the flow of DEC was cascaded to a liquid level of 88% (arbitrary scale) in to maintain a constant liquid level. The run was performed by continuously draining the reaction mixture in the reboiler, while pumping in 36.5 wt. % phenol solution in DEC. The result of the 234 hours time-on stream is listed in Table 2. The overhead stream was composed of mostly DEC., ethanol and small amounts of phenol and EPC. Samples were taken from the reboiler and overhead stream for analysis. Phenetole was the only by-product in the bottoms stream from reboiler. The result of this run in Table 2 clearly indicates slower deactivation and higher activity than the Catalyst A of the Test 6A.

The result of this run in Table 2 clearly indicates slower deactivation and higher activity of the Catalyst C than the Catalyst A.

The run was continued to 360 hours of on-stream time. Continued catalyst deactivation was observed. On stream time of 360 hours, the reactor operation for the synthesis of aromatic carbonate was terminated to perform catalyst regeneration. The catalyst regeneration was performed at 340° F. and 230 psig by depolymerizing polymers on the catalyst by circulating ethanol through the reactor for 17 hours. The major products of depolymerization reaction with ethanol were phenol, DEC and unidentified by products. The run was resumed with the regenerated catalyst. The test result of the regenerated catalyst is listed in Table 3.

The result in Table 3 clearly demonstrates that the catalyst can be regenerated by performing depolymerization of the polymers deposited on the catalyst.

TABLE 2

| | Hours on stream time | | | | | |
|---|---|---|---|---|---|---|
| | 33 | 56 | 94 | 160 | 216 | 234 |
| Phenol conversion (m %) | 23.5 | 38.5 | 34.7 | 31.9 | 29.1 | 25.0 |
| EPC productivity (m/h/kg) | 0.686 | 1.119 | 1.027 | 0.976 | 0.556 | 0.510 |
| DPC productivity (m/h/kg) | 0.008 | 0.020 | 0.019 | 0.019 | 0.012 | 0.012 |
| Phenetole productivity (m/h/kg) | .0018 | 0.0019 | 0.0014 | 0.011 | 0.0006 | 0.0006 |

TABLE 3

Catalyst Regeneration

| | Hours of on stream time: | | |
|---|---|---|---|
| | 360 | 393 | 428 |
| The overhead cot press(psig): | 18.2 | 19.5 | 18.1 |
| Reboiler temp (° F.): | 347 | 344 | 344 |
| Distillation cot temp (° F.): | 273-285 | 273-286 | 271-285 |
| Recirculation rate (ml/min): | 65 | 66 | 67 |
| Press at top of reactor (psig): | 20 | 22.2 | 20.4 |
| Press at btm of reactor (psig): | 19.2 | 22.1 | 20 |
| Fixed bed reactor temp (° F.): | 330-330 | 330-331 | 331-330 |
| PhOH/DEC soln flow rate (ml/min): | 0.18 | 0.18 | 0.18 |
| Btm flow rate (ml/min): | 0.16 | 0.18 | 0.18 |
| Phenol Conversion (m %): | 17.5 | 23.4 | 27.2 |
| EPC Yield (m %): | 16.47 | 22.8 | 26.2 |
| DPC Yield (m %): | 0.95 | 0.610 | 1.017 |
| EPC selectivity (m %): | 94.35 | 97.3 | 96.3 |
| DPC Selectivity (m %): | 5.44 | 2.60 | 3.73 |
| Phenetole Selectivity (m %): | 0.21 | 0.13 | 0.10 |
| EPC Productivity (m/h/kg): | 0.452 | 0.681 | 0.830 |
| DPC Productivity (m/h/kg): | 0.013 | 0.009 | 0.016 |

The invention claimed is:

1. A process of the production of diaryl carbonate comprising:
   (a) a plurality of reaction zones comprising a primary and a secondary reaction zone;
   (b) supplying to said primary reaction zone a dialkyl carbonate and an aromatic hydroxy compound;
   (c) maintaining the primary reaction zone under dual phase and reaction conditions conducive for the formation of alkyl aryl carbonate;
   (d) transesterifying the dialkyl carbonate with the aromatic hydroxy compound in the presence of a solid catalyst selected from the group consisting of two to four elements from Group IV, V and VI of the Periodic Table supported on porous material which have surface hydroxyl groups;
   (e) recovering a dual phase product stream from the primary reaction zone;
   (f) seperating the dual phase product stream from (e) to recover vaporous alkyl alcohol and liquid alkyl aryl carbonate;
   (g) maintaining the secondary reaction zone under dual phase and reaction conditions conducive for the disproportionation of alkyl aryl carbonate to diaryl carbonate;
   (h) disproportionating the alkyl aryl carbonate in the presence of a solid catalyst selected from the group consisting of two to four elements from Group IV, V and VI of the Periodic Table on porous material which have surface hydroxyl groups;
   (i) recovering a dual phase product stream from the secondary reaction zone; and
   (j) seperating the dual phase product stream from (i) to recover a vaporous component comprising aryl alkyl carbonate and liquid product comprising diaryl carbonate.

2. The process according to claim 1 wherein the dialkyl carbonate is DEC, the aromatic hydroxy compound is phenol, the alkyl aryl carbonate is EPC and diaryl carbonate is DPC.

3. The process according to claim 2 wherein the alkyl carbonate is DEC, the alkyl aryl carbonate is EPC and the aromatic hydroxy compound is phenol.

4. The process according to claim 3 wherein in (h) the mole ratio of phenol to DPC is in the range of 0.05 to 10.

5. The process according to claim 1 wherein in the solid catalyst of (d) is oxides, hydroxides, oxyhydroxides, alkoxides or mixtures thereof of elements from Groups IV, V and VI.

6. The process according to claim 5 wherein in the support comprises treated silica.

7. The process according to claim 5 wherein in the solid catalyst of (h) is oxides, hydroxides, oxyhydroxides, alkoxides or mixtures thereof of elements from Groups IV, V and VI.

8. The process according to claim 6 wherein in the solid catalyst of (d) is selected from the group consisting of a metal alkoxide and mixed metal alkoxides of Group IV and V.

9. The process according to claim 5 wherein in the solid catalyst of is $TiO_2/Nb_2O_5$ supported on treated silica, said treated silica having less than 0.05 wt. % Na.

10. The process according to claim 1 wherein in the solid catalyst of (h) is oxides, hydroxides, oxyhydroxides, alkoxides or mixtures thereof of elements from Groups IV, V and VI.

11. The process according to claim 10 wherein in the support comprises treated silica.

12. The process according to claim 11 wherein in the solid catalyst of (h) is oxides, hydroxides, oxyhydroxides, alkoxides or mixtures thereof of elements from Groups IV, V and VI.

13. The process according to claim 12 wherein in the solid catalyst of (h) is selected from the group consisting of a metal alkoxide and mixed metal alkoxides of Group IV and V.

14. The process according to claim 10 wherein in the solid catalyst of (h) is $TiO_2/Nb_2O_5$ supported on treated silica, said treated silica having less than 0.05 wt. % Na.

15. The process according to claim 1 wherein (h) is carried out in the presence of an aromatic hydroxy compound in a mole ratio of aromatic hydroxy compound to DPC in the range of 0.05:1 to 10:1.

16. The process according to claim 15 wherein (h) is carried out in the presence of a trace amount of water in an amount of up to 0.3 wt %.

17. The process according to claim 1 wherein (d) is carried out in the presence of an aromatic hydroxy compound in a mole ratio of aromatic hydroxy compound to DEC is above 0.2.

* * * * *

UNITED STATES PATENT AND TRADEMARK OFFICE
CERTIFICATE OF CORRECTION

PATENT NO. : 7,378,540 B2 Page 1 of 1
APPLICATION NO. : 11/256394
DATED : May 27, 2008
INVENTOR(S) : J. Yong Ryu It is certified that error appears in the above-identified patent and that said Letters Patent is hereby corrected as shown below:

In the Claims:

In Claim 9, column 20, line 51, after the word "of", insert -- (d) --.

Signed and Sealed this

Twenty-sixth Day of August, 2008

JON W. DUDAS
*Director of the United States Patent and Trademark Office*